United States Patent [19]

Sekiya et al.

[11] Patent Number: 5,126,483
[45] Date of Patent: Jun. 30, 1992

[54] 1-PHENYLALKYL-3-PHENYLUREA DERIVATIVES

[75] Inventors: Tetsuo Sekiya, Yokohama; Shinya Inoue, Tokyo; Chiaki Hyodo, Machida; Hiromi Okushima, Kawasaki; Kohei Umezu, Yokohama; Kazuo Suzuki, Machida, all of Japan

[73] Assignee: Mitsubishi Kasei Corporation, Tokyo, Japan

[21] Appl. No.: 562,337

[22] Filed: Aug. 3, 1990

[30] Foreign Application Priority Data

Aug. 4, 1989 [JP] Japan .................. 1-202422
Mar. 1, 1990 [JP] Japan .................. 2-50065
Jul. 13, 1990 [JP] Japan .................. 2-185845

[51] Int. Cl.⁵ .................................. C07C 275/28
[52] U.S. Cl. ........................... 564/48; 564/52; 564/53; 564/54; 564/56
[58] Field of Search ............ 564/48, 56, 52, 53, 54; 514/596, 588, 585

[56] References Cited

U.S. PATENT DOCUMENTS 4,623,662  11/1986  De Vries .................. 514/596

FOREIGN PATENT DOCUMENTS 10293880  7/1988  European Pat. Off. .
10297610  4/1989  European Pat. Off. .
20335374  4/1989  European Pat. Off. .
20335375  4/1989  European Pat. Off. .
20344425  6/1989  European Pat. Off. .

*Primary Examiner*—Glennon H. Hollrah
*Assistant Examiner*—Shailendra Kumar
*Attorney, Agent, or Firm*—Foley & Lardner

[57] ABSTRACT

Novel 1-phenylakyl-3-phenylurea derivatives represented by the following formula (I):

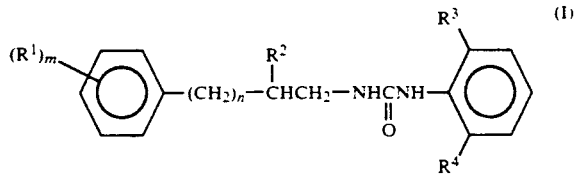

wherein $R^1$ is an alkyl group of 1 to 8 carbon atoms, an alkoxy group of 1 to 5 carbon atoms or a halogen atom, $R^2$ is an alkyl group of 1 to 15 carbon atoms, each of $R^3$ and $R^4$ is independently an alkyl group of 1 to 5 carbon atoms, m is an integer of 1 to 3, and n is 0 or 1, are provided.

The compounds are potent in reducing the cholesterol level in serum, and useful for treating hyperlipemia and atherosclerosis.

1 Claim, No Drawings

1-PHENYLALKYL-3-PHENYLUREA DERIVATIVES

FIELD OF THE INVENTION

The present invention relates to 1-phenylalkyl-3-phenylurea derivatives which are potent in reducing a lipid level in blood and, therefore, useful as therapeutical medicines for hyperlipemia and atherosclerosis.

BACKGROUND OF THE INVENTION

Heretofore, it has been considered that hyperlipemia caused by metabolic error of lipids results in arteriosclerosis and is one of the major dangerous factors causing ischemic heart disease or cerebral embolism Recently, it was revealed that an enzyme, acyl-CoA: cholesterol acyltransferase (ACAT) acts an important role at lipid metabolism, especially cholesterol metabolism. It was also reported that compounds having an inhibitory activity of the enzyme, ACAT, actually inhibit the absorption of cholesterol at intestine, reduce the level of cholesterol in blood, and inhibit the deposition of cholesterol on arterial wall, and accordingly, are useful as therapeutical medicines for atherosclerosis as well as hyperlipemia, as described in Japanese Patent Application Laying-Open (Kokai) No. 16761/88, No. 93569/89, No. 6455/90, No. 6456/90, and No. 457/90.

SUMMARY OF THE INVENTION

As a result of the extensive search for more potent compounds, the present inventors have found novel and useful 1-phenylalkyl-3-phenylurea derivatives which show an excellent lipid-reducing activity, and achieved the present invention.

Specifically, the present invention provides a 1-phenylalkyl-3-phenylurea derivative represented by the following formula (I):

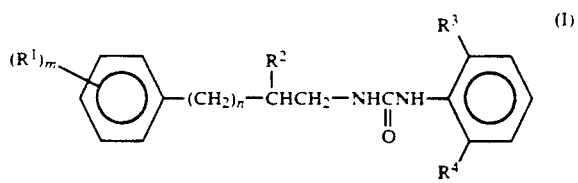

wherein $R^1$ is an alkyl group of 1 to 8 carbon atoms, an alkoxy group of 1 to 5 carbon atoms or a halogen atom, $R^2$ is an alkyl group of 1 to 15 carbon atoms, each of $R^3$ and $R^4$ is independently an alkyl group of 1 to 5 carbon atoms, m is an integer of 1 to 3, and n is 0 or 1.

The compounds according to the invention are potent in reducing the cholesterol level in blood owing to the ACAT inhibition, and accordingly, useful for treating hyperlipemia and/or atherosclerosis.

DETAILED DESCRIPTION OF THE PREFERRED EMBODIMENTS

The 1-phenylalkyl-3-phenylurea derivative according to the present invention is represented by the above formula (I).

The examples of $R^1$ in the formula (I), i.e., an alkyl group of 1 to 8 carbon atoms, include methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, hexyl groups, heptyl groups, and octyl groups.

As the alkoxy group of 1 to 5 carbon atoms, there may be mentioned methoxy group, ethoxy group, n-propoxy group, isopropoxy group, n-butoxy group, isobutoxy group, sec-butoxy group, tert-butoxy group, n-pentoxy group, isopentoxy group, sec-pentoxy group, tert-pentoxy group, or neopentoxy group. Furthermore, as the halogen atom, there may be mentioned fluorine atom, chlorine atom, bromine atom, or iodine atom.

As the alkyl group of 1 to 15 carbon atoms of $R^2$, there may be mentioned methyl group, ethyl group, n-propyl group, isopropyl group, n-butyl group, isobutyl group, sec-butyl group, tert-butyl group, n-pentyl group, isopentyl group, sec-pentyl group, tert-pentyl group, neopentyl group, one of hexyl groups, one of heptyl groups, one of octyl groups, one of nonyl groups, one of decyl groups, one of undecyl groups, one of dodecyl groups, one of tridecyl groups, one of tetradecyl groups, or one of pentadecyl groups.

As the alkyl ethyl group of 1 to 5 carbon atoms of $R^3$ or $R^4$, there may be mentioned methyl group, ethyl group, n-proply group, isopropyl group, n-butyl group, isobutyl group, sec-butyl group, tert-butyl group, n-pentyl group, isopentyl group, sec-pentyl group, tert-pentyl group, or neopentyl group.

In the formula (I), $R^2$ may preferably be a normal alkyl group of 4 to 6 carbon atoms, and, in this case, more preferably, each of $R^3$ and $R^4$ is the same alkyl group of 1 to 3 carbon atoms.

The examples of the compounds according to the present invention are illustrated in the following Table. The compounds of the invention possesses at least one asymmetric carbon and may be racemic or optically pure.

| $(R^1)_m$ | n | $R^2$ | $R^3$ | $R^4$ |
|---|---|---|---|---|
| 2-CH$_3$ | 0 | -n-C$_4$H$_9$ | —C$_2$H$_5$ | —C$_2$H$_5$ |
| 2-CH$_3$ | 0 | -n-C$_4$H$_9$ | -i-C$_3$H$_7$ | -i-C$_3$H$_7$ |
| 2-CH$_3$ | 0 | -n-C$_5$H$_{11}$ | —C$_2$H$_5$ | —C$_2$H$_5$ |
| 2-CH$_3$ | 0 | -n-C$_5$H$_{11}$ | -i-C$_3$H$_7$ | -i-C$_3$H$_7$ |
| 2-CH$_3$ | 0 | -i-C$_5$H$_{11}$ | —C$_2$H$_5$ | —C$_2$H$_5$ |
| 2-CH$_3$ | 0 | -i-C$_5$H$_{11}$ | -i-C$_3$H$_7$ | -i-C$_3$H$_7$ |
| 2-CH$_3$ | 0 | -n-C$_6$H$_{13}$ | —C$_2$H$_5$ | —C$_2$H$_5$ |
| 2-CH$_3$ | 0 | -n-C$_6$H$_{13}$ | -i-C$_3$H$_7$ | -i-C$_3$H$_7$ |
| 2-CH$_3$ | 0 | -i-C$_6$H$_{13}$ | —C$_2$H$_5$ | —C$_2$H$_5$ |
| 2-CH$_3$ | 0 | -i-C$_6$H$_{13}$ | -i-C$_3$H$_7$ | -i-C$_3$H$_7$ |
| 2-C$_2$H$_5$ | 0 | -n-C$_4$H$_9$ | —C$_2$H$_5$ | —C$_2$H$_5$ |
| 2-C$_2$H$_5$ | 0 | -n-C$_4$H$_9$ | -i-C$_3$H$_7$ | -i-C$_3$H$_7$ |
| 2-C$_2$H$_5$ | 0 | -n-C$_5$H$_{11}$ | —C$_2$H$_5$ | —C$_2$H$_5$ |
| 2-C$_2$H$_5$ | 0 | -n-C$_5$H$_{11}$ | -i-C$_3$H$_7$ | -i-C$_3$H$_7$ |
| 2-C$_2$H$_5$ | 0 | -i-C$_5$H$_{11}$ | —C$_2$H$_5$ | —C$_2$H$_5$ |
| 2-C$_2$H$_5$ | 0 | -i-C$_5$H$_{11}$ | -i-C$_3$H$_7$ | -i-C$_3$H$_7$ |
| 2-C$_2$H$_5$ | 0 | -n-C$_6$H$_{13}$ | —C$_2$H$_5$ | —C$_2$H$_5$ |
| 2-C$_2$H$_5$ | 0 | -n-C$_6$H$_{13}$ | -i-C$_3$H$_7$ | -i-C$_3$H$_7$ |
| 2-C$_2$H$_5$ | 0 | -i-C$_6$H$_{13}$ | —C$_2$H$_5$ | —C$_2$H$_5$ |
| 2-C$_2$H$_5$ | 0 | -i-C$_6$H$_{13}$ | -i-C$_3$H$_7$ | -i-C$_3$H$_7$ |
| 2-n-C$_3$H$_7$ | 0 | -n-C$_4$H$_9$ | -i-C$_3$H$_7$ | -i-C$_3$H$_7$ |
| 2-n-C$_3$H$_7$ | 0 | -n-C$_5$H$_{11}$ | -i-C$_3$H$_7$ | -i-C$_3$H$_7$ |
| 2-n-C$_3$H$_7$ | 0 | -i-C$_5$H$_{11}$ | -i-C$_3$H$_7$ | -i-C$_3$H$_7$ |
| 2-i-C$_3$H$_7$ | 0 | -n-C$_4$H$_9$ | -i-C$_3$H$_7$ | -i-C$_3$H$_7$ |
| 2-i-C$_3$H$_7$ | 0 | -n-C$_5$H$_{11}$ | -i-C$_3$H$_7$ | -i-C$_3$H$_7$ |
| 2-n-C$_4$H$_9$ | 0 | -n-C$_4$H$_9$ | -i-C$_3$H$_7$ | -i-C$_3$H$_7$ |

-continued

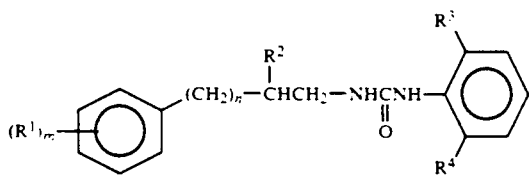

| $(R^1)_m$ | n | $R^2$ | $R^3$ | $R^4$ |
|---|---|---|---|---|
| 3-CH₃ | 0 | -n-C₄H₉ | —C₂H₅ | —C₂H₅ |
| 3-CH₃ | 0 | -n-C₄H₉ | -i-C₃H₇ | -i-C₃H₇ |
| 3-CH₃ | 0 | -n-C₅H₁₁ | —C₂H₅ | —C₂H₅ |
| 3-CH₃ | 0 | -n-C₅H₁₁ | -i-C₃H₇ | -i-C₃H₇ |
| 3-CH₃ | 0 | -n-C₆H₁₃ | —C₂H₅ | —C₂H₅ |
| 3-CH₃ | 0 | -n-C₆H₁₃ | -i-C₃H₇ | -i-C₃H₇ |
| 3-CH₃ | 0 | -i-C₆H₁₃ | -i-C₃H₇ | -i-C₃H₇ |
| 3-C₂H₅ | 0 | -n-C₄H₉ | —C₂H₅ | —C₂H₅ |
| 3-C₂H₅ | 0 | -n-C₄H₉ | -i-C₃H₇ | -i-C₃H₇ |
| 3-C₂H₅ | 0 | -n-C₅H₁₁ | -i-C₃H₇ | -i-C₃H₇ |
| 3-C₂H₅ | 0 | -i-C₅H₁₁ | -i-C₃H₇ | -i-C₃H₇ |
| 3-n-C₃H₇ | 0 | -n-C₄H₉ | -i-C₃H₇ | -i-C₃H₇ |
| 3-i-C₃H₇ | 0 | -n-C₄H₉ | -i-C₃H₇ | -i-C₃H₇ |
| 3-n-C₄H₉ | 0 | -n-C₄H₉ | -i-C₃H₇ | -i-C₃H₇ |
| 3-n-C₅H₁₁ | 0 | -n-C₄H₉ | -i-C₃H₇ | -i-C₃H₇ |
| 4-CH₃ | 0 | -n-C₄H₉ | -i-C₃H₇ | -i-C₃H₇ |
| 4-CH₃ | 0 | -n-C₅H₁₁ | -i-C₃H₇ | -i-C₃H₇ |
| 4-C₂H₅ | 0 | -n-C₄H₉ | -i-C₃H₇ | -i-C₃H₇ |
| 4-n-C₃H₇ | 0 | -n-C₄H₉ | -i-C₃H₇ | -i-C₃H₇ |
| 4-i-C₃H₇ | 0 | -n-C₄H₉ | -i-C₃H₇ | -i-C₃H₇ |
| 4-n-C₄H₉ | 0 | -n-C₄H₉ | -i-C₃H₇ | -i-C₃H₇ |
| 4-n-C₅H₁₁ | 0 | -n-C₄H₉ | -i-C₃H₇ | -i-C₃H₇ |
| 4-n-C₅H₁₁ | 0 | -n-C₄H₉ | -i-C₃H₇ | -i-C₃H₇ |
| 2,3-diCH₃ | 0 | —CH₃ | —CH₃ | —CH₃ |
| 2,3-diCH₃ | 0 | —C₂H₅ | -i-C₃H₇ | -i-C₃H₇ |
| 2,3-diCH₃ | 0 | -n-C₃H₇ | —C₂H₅ | —C₂H₅ |
| 2,3-diCH₃ | 0 | -n-C₃H₇ | -i-C₃H₇ | -i-C₃H₇ |
| 2,3-diCH₃ | 0 | -i-C₃H₇ | -i-C₃H₇ | -i-C₃H₇ |
| 2,3-diCH₃ | 0 | -n-C₄H₉ | —CH₃ | —CH₃ |
| 2,3-diCH₃ | 0 | -n-C₄H₉ | —C₂H₅ | —C₂H₅ |
| 2,3-diCH₃ | 0 | -n-C₄H₉ | —C₂H₅ | -n-C₃H₇ |
| 2,3-diCH₃ | 0 | -n-C₄H₉ | —C₂H₅ | -i-C₃H₇ |
| 2,3-diCH₃ | 0 | -n-C₄H₉ | —C₂H₅ | -sec-C₄H₉ |
| 2,3-diCH₃ | 0 | -n-C₄H₉ | -i-C₃H₇ | -i-C₃H₇ |
| 2,3-diCH₃ | 0 | -n-C₅H₁₁ | —C₂H₅ | —C₂H₅ |
| 2,3-diCH₃ | 0 | -n-C₅H₁₁ | -i-C₃H₇ | -i-C₃H₇ |
| 2,3-diCH₃ | 0 | -i-C₅H₁₁ | —C₂H₅ | —C₂H₅ |
| 2,3-diCH₃ | 0 | -i-C₅H₁₁ | -i-C₃H₇ | -i-C₃H₇ |
| 3,4-diCH₃ | 0 | -n-C₄H₉ | -i-C₃H₇ | -i-C₃H₇ |
| 2,3,4-triCH₃ | 0 | -n-C₄H₉ | —C₂H₅ | —C₂H₅ |
| 2,3,4-triCH₃ | 0 | -n-C₄H₉ | -i-C₃H₇ | -i-C₃H₇ |
| 2,3,4-triCH₃ | 0 | -n-C₅H₁₁ | —C₂H₅ | —C₂H₅ |
| 2,3,4-triCH₃ | 0 | -n-C₅H₁₁ | -i-C₃H₇ | -i-C₃H₇ |
| 2-OCH₃ | 0 | -n-C₄H₉ | —C₂H₅ | —C₂H₅ |
| 2-OCH₃ | 0 | -n-C₄H₉ | -i-C₃H₇ | -i-C₃H₇ |
| 2-OCH₃ | 0 | -n-C₅H₁₁ | —C₂H₅ | —C₂H₅ |
| 2-OCH₃ | 0 | -n-C₅H₁₁ | -i-C₃H₇ | -i-C₃H₇ |
| 2-OCH₃ | 0 | -n-C₆H₁₃ | —C₂H₅ | —C₂H₅ |
| 2-OCH₃ | 0 | -n-C₆H₁₃ | -i-C₃H₇ | -i-C₃H₇ |
| 3-OCH₃ | 0 | -n-C₄H₉ | —C₂H₅ | —C₂H₅ |
| 3-OCH₃ | 0 | -n-C₄H₉ | -i-C₃H₇ | -i-C₃H₇ |
| 3-OCH₃ | 0 | -n-C₅H₁₁ | —C₂H₅ | —C₂H₅ |
| 3-OCH₃ | 0 | -n-C₅H₁₁ | -i-C₃H₇ | -i-C₃H₇ |
| 3-OCH₃ | 0 | -n-C₆H₁₃ | —C₂H₅ | —C₂H₅ |
| 3-OCH₃ | 0 | -n-C₆H₁₃ | -i-C₃H₇ | -i-C₃H₇ |
| 3-OCH₃ | 0 | -i-C₆H₁₃ | -i-C₃H₇ | -i-C₃H₇ |
| 4-OCH₃ | 0 | -n-C₄H₉ | -i-C₃H₇ | -i-C₃H₇ |
| 4-OCH₃ | 0 | -n-C₅H₁₁ | -i-C₃H₇ | -i-C₃H₇ |
| 2,3-diOCH₃ | 0 | -n-C₄H₉ | -n-C₃H₇ | -n-C₃H₇ |
| 2,3-diOCH₃ | 0 | -n-C₄H₉ | -i-C₃H₇ | -i-C₃H₇ |
| 2,3-diOCH₃ | 0 | -n-C₅H₁₁ | —C₂H₅ | —C₂H₅ |
| 2,3-diOCH₃ | 0 | -n-C₅H₁₁ | -i-C₃H₇ | -i-C₃H₇ |
| 2,3-diOCH₃ | 0 | -sec-C₅H₁₁ | -i-C₃H₇ | -i-C₃H₇ |
| 2,3-diOCH₃ | 0 | -i-C₅H₁₁ | -i-C₃H₇ | -i-C₃H₇ |
| 2,3-diOCH₃ | 0 | -n-C₆H₁₃ | —C₂H₅ | —C₂H₅ |
| 2,3-diOCH₃ | 0 | -n-C₇H₁₅ | -i-C₃H₇ | -i-C₃H₇ |
| 2,3-diOCH₃ | 0 | -n-C₈H₁₇ | -i-C₃H₇ | -i-C₃H₇ |
| 2,3-diOCH₃ | 0 | -n-C₉H₁₉ | -i-C₃H₇ | -i-C₃H₇ |
| 2,3-diOCH₃ | 0 | -n-C₁₀H₂₁ | -i-C₃H₇ | -i-C₃H₇ |
| 2,3-diOCH₃ | 0 | -n-C₁₁H₂₃ | -i-C₃H₇ | -i-C₃H₇ |
| 2,3-diOCH₃ | 0 | -n-C₁₂H₂₅ | -i-C₃H₇ | -i-C₃H₇ |

-continued

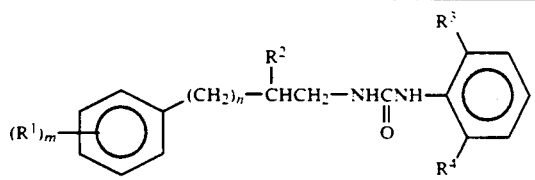

| $(R^1)_m$ | n | $R^2$ | $R^3$ | $R^4$ |
|---|---|---|---|---|
| 2,3-diOCH₃ | 0 | -n-C₁₃H₂₇ | -i-C₃H₇ | -i-C₃H₇ |
| 2,3-diOCH₃ | 0 | -n-C₁₄H₂₉ | -i-C₃H₇ | -i-C₃H₇ |
| 2,3-diOCH₃ | 0 | -n-C₁₅H₃₁ | -i-C₃H₇ | -i-C₃H₇ |
| 3,4-diOCH₃ | 0 | -n-C₄H₉ | —C₂H₅ | —C₂H₅ |
| 3,4-diOCH₃ | 0 | -n-C₄H₉ | -i-C₃H₇ | -i-C₃H₇ |
| 3,4-diOCH₃ | 0 | -n-C₅H₁₁ | —C₂H₅ | —C₂H₅ |
| 3,4-diOCH₃ | 0 | -n-C₅H₁₁ | -i-C₃H₇ | -i-C₃H₇ |
| 3,4-diOCH₃ | 0 | -i-C₅H₁₁ | —C₂H₅ | —C₂H₅ |
| 3,4-diOCH₃ | 0 | -i-C₅H₁₁ | -i-C₃H₇ | -i-C₃H₇ |
| 3,4-diOCH₃ | 0 | -n-C₆H₁₃ | —C₂H₅ | —C₂H₅ |
| 3,4-diOCH₃ | 0 | -n-C₆H₁₃ | -i-C₃H₇ | -i-C₃H₇ |
| 3,4-diOCH₃ | 0 | -i-C₆H₁₃ | —C₂H₅ | —C₂H₅ |
| 3,4-diOCH₃ | 0 | -i-C₆H₁₃ | -i-C₃H₇ | -i-C₃H₇ |
| 2-F | 0 | -n-C₄H₉ | -i-C₃H₇ | -i-C₃H₇ |
| 2-F | 0 | -n-C₅H₁₁ | -i-C₃H₇ | -i-C₃H₇ |
| 3-F | 0 | -n-C₄H₉ | -i-C₃H₇ | -i-C₃H₇ |
| 3-F | 0 | -n-C₅H₁₁ | -i-C₃H₇ | -i-C₃H₇ |
| 4-F | 0 | -n-C₄H₉ | -i-C₃H₇ | -i-C₃H₇ |
| 4-F | 0 | -n-C₅H₁₁ | -i-C₃H₇ | -i-C₃H₇ |
| 2-Cl | 0 | -n-C₄H₉ | —C₂H₅ | —C₂H₅ |
| 2-Cl | 0 | -n-C₄H₉ | -i-C₃H₇ | -i-C₃H₇ |
| 2-Cl | 0 | -n-C₅H₁₁ | —C₂H₅ | —C₂H₅ |
| 2-Cl | 0 | -n-C₅H₁₁ | -i-C₃H₇ | -i-C₃H₇ |
| 2-Cl | 0 | -n-C₆H₁₃ | -i-C₃H₇ | -i-C₃H₇ |
| 3-Cl | 0 | -n-C₄H₉ | —C₂H₅ | —C₂H₅ |
| 3-Cl | 0 | -n-C₄H₉ | -i-C₃H₇ | -i-C₃H₇ |
| 3-Cl | 0 | -n-C₅H₁₁ | —C₂H₅ | —C₂H₅ |
| 3-Cl | 0 | -n-C₅H₁₁ | -i-C₃H₇ | -i-C₃H₇ |
| 3-Cl | 0 | -n-C₆H₁₃ | —C₂H₅ | —C₂H₅ |
| 3-Cl | 0 | -n-C₆H₁₃ | -i-C₃H₇ | -i-C₃H₇ |
| 4-Cl | 0 | -n-C₄H₉ | -i-C₃H₇ | -i-C₃H₇ |
| 4-Cl | 0 | -n-C₅H₁₁ | -i-C₃H₇ | -i-C₃H₇ |
| 2-Br | 0 | -n-C₄H₉ | -i-C₃H₇ | -i-C₃H₇ |
| 2-Br | 0 | -n-C₅H₁₁ | -i-C₃H₇ | -i-C₃H₇ |
| 3-Br | 0 | -n-C₄H₉ | -i-C₃H₇ | -i-C₃H₇ |
| 3-Br | 0 | -n-C₅H₁₁ | -i-C₃H₇ | -i-C₃H₇ |
| 4-Br | 0 | -n-C₄H₉ | -i-C₃H₇ | -i-C₃H₇ |
| 4-Br | 0 | -n-C₅H₁₁ | -i-C₃H₇ | -i-C₃H₇ |
| 2-I | 0 | -n-C₄H₉ | -i-C₃H₇ | -i-C₃H₇ |
| 2-I | 0 | -n-C₅H₁₁ | -i-C₃H₇ | -i-C₃H₇ |
| 3-I | 0 | -n-C₄H₉ | -i-C₃H₇ | -i-C₃H₇ |
| 3-I | 0 | -n-C₅H₁₁ | -i-C₃H₇ | -i-C₃H₇ |
| 4-I | 0 | -n-C₄H₉ | -i-C₃H₇ | -i-C₃H₇ |
| 4-I | 0 | -n-C₅H₁₁ | -i-C₃H₇ | -i-C₃H₇ |
| 2-CH₃ | 1 | -n-C₄H₉ | -i-C₃H₇ | -i-C₃H₇ |
| 3-CH₃ | 1 | -n-C₄H₉ | -i-C₃H₇ | -i-C₃H₇ |
| 4-CH₃ | 1 | -n-C₄H₉ | -i-C₃H₇ | -i-C₃H₇ |
| 2-Cl | 1 | -n-C₄H₉ | -i-C₃H₇ | -i-C₃H₇ |
| 3-Cl | 1 | -n-C₄H₉ | -i-C₃H₇ | -i-C₃H₇ |
| 4-Cl | 1 | -n-C₄H₉ | -i-C₃H₇ | -i-C₃H₇ |

It should be, however, understood that the present invention is not limited to the above examples.

The compounds of the present invention may be prepared, for example, according to the processes described below.

Method A

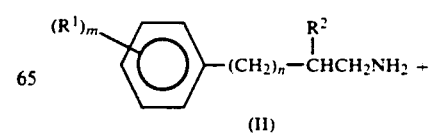

-continued

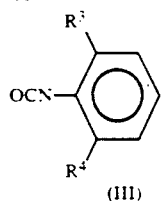

wherein, $R^1$, $R^2$, $R^3$, $R^4$, m and n are the same as defined above.

According to Method A, the compound (I) of the invention is prepared by condensing a phenylalkylamine derivative of the formula (II) with a phenyl isocyanate derivative of the formula (III) at a temperature range of 0° C. to 150° C. in an inert solvent such as benzene, toluene, xylene, hexane, heptane, diethyl ether, tetrahydrofuran (THF), dioxane, or N,N-dimethylformamide.

Method B

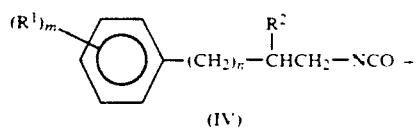

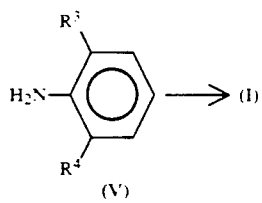

wherein, $R^1$, $R^2$, $R^3$, $R^4$, m and n are the same as defined above.

According to method B, the compound (I) of the invention is prepared by reacting a phenylalkyl isocyanate of the formula (IV) with an aniline derivative of the formula (V) in a similar manner to method A.

Method C

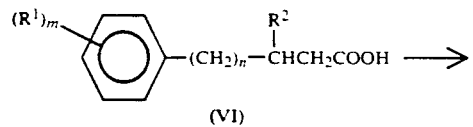

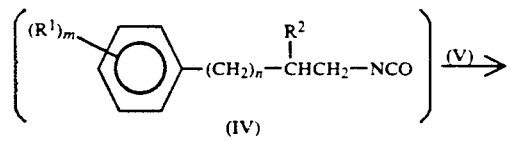

wherein, $R^1$, $R^2$, $R^3$, $R^4$, m and n are the same as defined above.

This method is basically similar to Method B. Thus, the compound (I) of the invention is prepared by converting a phenylalkylcarboxylic acid derivative of the formula (VI) into a phenylalkyl isocyanate derivative of the formula (IV), followed by condensing the isocyanate derivative (IV) with an aniline derivative of the formula (V). The conversion of the phenylalkylcarboxylic acid derivative of the formula (VI) into the phenylalkyl isocyanate derivative of the formula (IV) may be achieved, for example, by treating the phenylalkylcarboxylic acid derivative with DPPA (diphenoxy phosphoryl azide) in the presence of an inert amine such as triethylamine at a temperature range of room temperature to 150° C. in an inert solvent such as benzene, toluene or xylene.

Method D

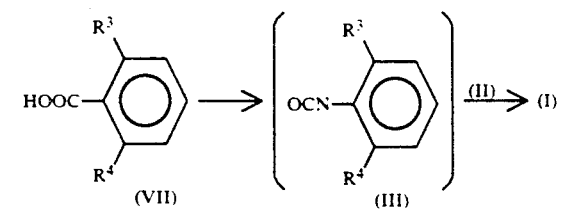

wherein, $R^3$ and $R^4$ are the same as defined above.

Method D comprises the preparation of the compound (I) of the invention by converting a benzoic acid derivative of the formula (VII) into a phenyl isocyanate derivative of the formula (III) in an similar manner to Method C, followed by reacting the isocyanate derivative (III) with a phenylalkylamine derivative of the formula (II).

Method E

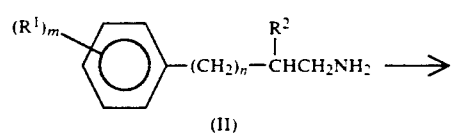

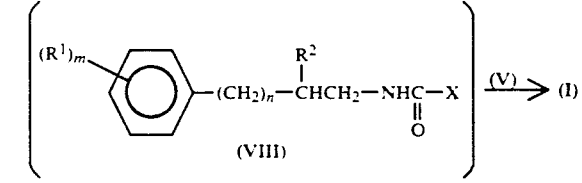

wherein, $R^1$, $R^2$, $R^3$, $R^4$, m and n are the same as defined above, and X is a leaving group such as a halogen atom, aryloxy group or alkylthio group.

Method E comprises the preparation of the compound (I) of the invention by converting a phenylalkylamine derivative of the formula (II) into a reactive intermediate of the formula (VIII), followed by reacting the resulting intermediate with an aniline derivative of the formula (V) at a temperature range of 0° C. to 150° C. in an inert solvent such as benzene, diethyl ether, or ethyl acetate. As the reactive intermediate, there may be mentioned a phenylalkylcarbamoyl chloride of the formula (VIII) in which X is chlorine atom obtained by reacting a phenylalkylamine derivative (II) with phosgene, or an aryl phenylalkylcarbamate of the formula (VIII) in which X is an aryloxy group, obtained by reacting a phenylalkylamine derivative (II) with an aryl chloroformate.

Method F

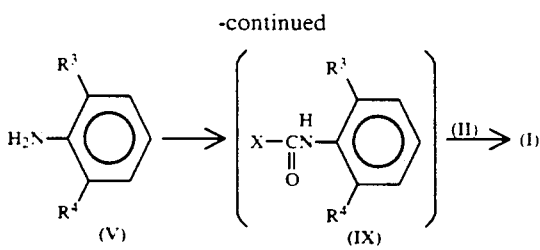

wherein, $R^3$, $R^4$ and X are the same as defined above.

Method F comprises the preparation of the compound (I) of the invention by converting an aniline derivative of the formula (V) into a reactive intermediate of the formula (IX), followed by reacting the intermediate with a phenylalkylamine derivative of the formula (II) at a temperature range of 0° C. to 150° C. in an inert solvent such as benzene, diethyl ether, or ethyl acetate. As the reactive intermediate, there may be mentioned a phenylcarbamoyl chloride of the formula (IX) in which X is chlorine atom obtained by reacting an aniline derivative (V) with phosgene, or an aryl phenylcarbamate of the formula (IX) in which X is an aryloxy group, obtained by reacting an aniline derivative (V) with an aryl chloroformate.

The present invention also provides an acyl-CoA: cholesterol acyltransferase inhibitor comprising a 1-phenylalkyl-3-phenylurea derivative as defined hereinbefore as active ingredient. The inhibitor may be administrated, preferably, orally to a human patient.

The present invention further provides a pharmaceutical composition for treating hyperlipemia and atherosclerosis comprising a therapeutically effective amount of a 1-phenylalkyl-3-phenylurea derivative as defined hereinbefore, in admixture with a pharmaceutically acceptable carrier, diluent or a mixture thereof. The composition may be administrated, preferably, orally to a patient.

The formulation for the oral administration may be tablet, granule, powder, capsule, etc. The inhibitor or pharmaceutical composition may further include usual additives known in the art, for example, an excipient such as glucose, lactose, corn starch or mannitol, a binder such as hydroxypropyl cellulose (HPC) and carboxymethyl cellulose (CMC), a disintegrating agent such as starch or powdery gelatin, a lubricating agent such as talc or magnesium stearate.

The dose of the compound according to the present invention, in the case of oral administration, is from 1 mg to 1000 mg per day for an adult, which may vary depending on the body conditions and necessity of patients, degree of the disease to be treated, and the activity of the compound used.

EXAMPLES

The present invention is further illustrated in detail with reference to the following examples. It should be understood that the present invention is not limited solely to those examples.

EXAMPLE 1

Preparation of 1-(2-(3-methylphenyl)hexyl)-3-(2,6-diisopropylphenyl)urea

To 20 ml of n-hexane was added 1.81 g (9.5 mmol) of 2-(3-methylphenyl)hexylamine. An 18 ml of 0.52M hexane solution of 2,6-diisopropylphenyl isocyanate was added dropwise to the mixture under ice cooling. The resulting mixture was stirred overnight and the precipitated crystals were collected by filtration to give 1.87 g (50% yield) of 1-(2-(3-methylphenyl)hexyl)-3-(2,6-diisopropylphenyl)urea.

Melting point: 173°–174° C.

IR (KBr) cm$^{-1}$: 3340, 2970, 1635, 1575, 1460, 1250, 700

NMR (CDCl$_3$) δ: 0.80 (t, 3H), 0.96–1.25 (m, 16H), 1.50–1.68 (m, 2H), 2.21 (s, 3H), 2.53 (m, 1H), 3.02–3.12 (m, 3H), 3.56 (m, 1H), 3.93 (br. s, 1H), 5.65 (s, 1H), 6.71 (m, 2H), 6.90 (d, 1H), 6.99–7.10 (m, 3H), 7.27 (t, 1H)

EXAMPLES 2–49

The compounds listed in Table 1-1, Table 1-2 and Table 1-3 were similarly prepared as described in Example 1. In the case that crystals were not precipitated from the reaction mixture during the operations similar to Example 1, the resulting crude products were purified by subjecting them to column chromatography over silica gel (eluent n-hexane/ethyl acetate =4/1) to give desired products.

In the tables, Me, Et, Pr, Bu, Pen, Hex, Hep, and Oct represent methy group, ethyl group, propyl group, pentyl group, hexyl group, heptyl group, and octyl group, respectively.

TABLE 1-1

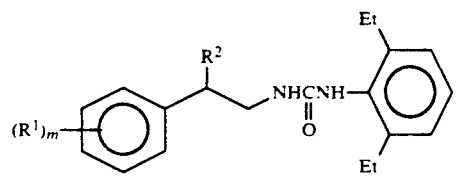

| Example No. | $(R^1)_m$ | $R^2$ | Yield (%) | Melting point (°C.) | IR(KBr)cm$^{-1}$ |
|---|---|---|---|---|---|
| 2 | 2-Me | n-Pen | 38 | 140–141 | 3300, 2950, 1630, 1560, 1460, 1250, 760 |
| 3 | 2-Me | n-Hex | 54 | 123–124 | 3300, 2900, 1630, 1560, 1450, 1250, 750 |
| 4 | 3-Me | n-Pen | 34 | 86–87 | 3320, 2950, 1630, 1565, 1460, 1250, 700 |
| 5 | 3-Me | n-Hex | 24 | amorphous | 3350, 2960, 1635, 1570, 1470, 1260, 710 |
| 6 | 3-OMe | n-Bu | 60 | amorphous | 3320, 2950, 1635, 1560, 1460, 1250, 1040, 700 |
| 7 | 3-OMe | n-Pen | 49 | amorphous | 3320, 2940, 1630, 1560, 1460, 1255, 1045, 700 |
| 8 | 3-OMe | n-Hex | 55 | amorphous | 3320, 2940, 1630, 1570, 1460, 1260, 1045, 700 |

TABLE 1-2

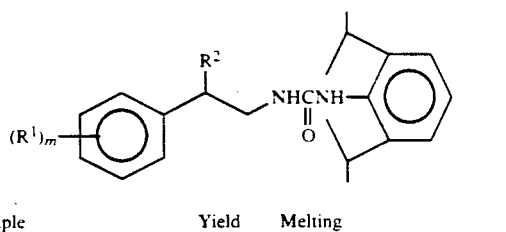

| Example No. | (R¹)ₘ | R² | Yield (%) | Melting point (°C.) | IR(KBr)cm⁻¹ |
|---|---|---|---|---|---|
| 9 | 2-Me | n-Bu | 50 | 121–123 | 3350, 2950, 1630, 1565, 1460, 1250, 800 |
| 10 | 2-Me | n-Pen | 27 | 120–122 | 3300, 2920, 1630, 1560, 1450, 1250, 750 |
| 11 | 2-Me | n-Hex | 51 | amorphous | 3300, 2950, 1630, 1560, 1460, 1250, 750 |
| 12 | 3-Me | n-Pen | 22 | 168–170 | 3300, 2960, 1630, 1565, 1460, 1250, 700 |
| 13 | 3-Me | n-Hex | 42 | 160–162 | 3350, 2950, 1630, 1565, 1460, 1260, 700 |
| 14 | 3-Me | i-Hex | 29 | 177–179 | 3300, 2950, 1630, 1560, 1460, 1250, 700 |
| 15 | 3-Et | n-Bu | 34 | 159–160 | 3340, 2960, 1630, 1570, 1460, 1250, 710 |
| 16 | 3-Pr | n-Bu | 37 | 140–141 | 3340, 2970, 1630, 1570, 1460, 1250, 810 |
| 17 | 3-Bu | n-Bu | 31 | 110–112 | 3350, 2950, 1630, 1560, 1460, 1250, 700 |
| 18 | 3-Hep | n-Bu | 63 | oil | 3330, 2950, 1620, 1560, 1460, 1250, 700 |
| 19 | 4-Me | n-Bu | 48 | 198–200 | 3340, 2950, 1630, 1565, 1460, 1250, 800 |
| 20 | 4-Bu | n-Bu | 71 | 136–137 | 3350, 2950, 1630, 1570, 1460, 1250, 800 |
| 21 | 3-Hep | n-Bu | 67 | oil | 3330, 2950, 1630, 1550, 1460, 1250, 800 |
| 22 | 2,3-diMe | n-Pen | 76 | 107–110 | 3340, 2980, 2950, 2900, 1640, 1570, 1530, 1470, 1260 |
| 23 | 3,4-diMe | n-Bu | 38 | 174–175 | 3300, 2920, 1630, 1560, 1450, 1250, 700 |
| 24 | 2,3,4-triMe | n-Bu | 22 | 144–146 | 3300, 2950, 1630, 1560, 1460, 1250, 800 |
| 25 | 2-OMe | n-Bu | 44 | 138–139 | 3300, 2960, 1630, 1560, 1460, 1240, 750 |
| 26 | 2-OMe | n-Pen | 44 | 134–136 | 3290, 2970, 1640, 1550, 1460, 1240, 750 |
| 27 | 2-OMe | n-Hex | 48 | 153–154 | 3250, 2950, 1640, 1550, 1460, 1240, 750 |
| 28 | 3-OMe | n-Bu | 55 | 159–161 | 3320, 2940, 1640, 1550, 1460, 1255, 1045, 700 |
| 29 | 3-OMe | n-Pen | 32 | 163–165 | 3320, 2940, 1635, 1565, 1460, 1260, 1050, 700 |
| 30 | 3-OMe | n-Hex | 53 | 131–133 | 3320, 2940, 1630, 1570, 1460, 1260, 1045, 700 |
| 31 | 3-OMe | i-Hex | 41 | 148–150 | 3330, 2960, 1630, 1565, 1460, 1260, 1050, 700 |
| 32 | 2,3-diOMe | n-Bu | 70 | 138–139 | 3450, 2950, 2880, 1645, 1550, 1480, 1270 |
| 33 | 2,3-diOMe | n-Pen | 47 | 152–154 | 3300, 2950, 1630, 1560, 1470, 1270, 750 |
| 34 | 3,4-diOMe | n-Bu | 72 | 131–133 | 3330, 2970, 1635, 1570, 1520, 1465, 1260, 1030 |
| 35 | 3,4-diOMe | n-Pen | 16 | amorphous | 3350, 2950, 1620, 1550, 1460, 1240, 800 |
| 36 | 3,4-diOMe | n-Hex | 19 | amorphous | 3350, 2950, 1630, 1560, 1460, 1250, 800 |
| 37 | 2-Cl | n-Bu | 10 | 118–119 | 3320, 2950, 1640, 1560, 1460, 1250, 750 |
| 38 | 2-Cl | n-Pen | 11 | 149–150 | 3300, 2920, 1630, 1560, 1460, 1250, 700 |
| 39 | 2-Cl | n-Hex | 13 | 131–132 | 3300, 2920, 1630, 1560, 1460, 1250, 750 |
| 40 | 3-Cl | n-Bu | 30 | 186–188 | 3350, 2970, 1630, 1570, 1460, 1250, 780, 700 |
| 41 | 3-Cl | n-Pen | 59 | 178–180 | 3320, 2990, 1630, 1570, 1460, 1250, 690 |
| 42 | 3-Cl | n-Hex | 40 | 161–164 | 3320, 2950, 1630, 1560, 1460, 1240, 750 |
| 43 | 4-Cl | n-Bu | 65 | 223–224 | 3350, 2980, 1635, 1575, 1500, 1280, 1015, 830 |

TABLE 1-3

| Example No. | (R¹)ₘ | R² | Yield (%) | Melting point (°C.) | IR(KBr)cm⁻¹ |
|---|---|---|---|---|---|
| 44 | 2-Me | n-Bu | 32 | 122–124 | 3330, 2950, 1630, 1560, 1460, 1250, 740 |
| 45 | 3-Me | n-Bu | 43 | 155–156 | 3330, 2950, 1630, 1560, 1460, 1250, 700 |
| 46 | 4-Me | n-Bu | 43 | amorphous | 3300, 2950, |

TABLE 1-3-continued

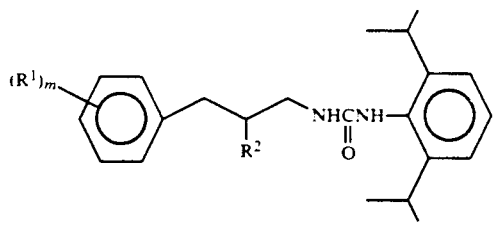

| Example No. | $(R^1)_m$ | $R^2$ | Yield (%) | Melting point (°C) | IR(KBr)cm$^{-1}$ |
|---|---|---|---|---|---|
| 47 | 2-Cl | n-Bu | 42 | 162-164 | 1630, 1560 1460, 1250, 800 3300, 2950, 1630, 1560 |
| 48 | 3-Cl | n-Bu | 28 | 140-142 | 1460, 1250, 750 3300, 2930, 1630, 1560 |
| 49 | 4-Cl | n-Bu | 29 | 170-171 | 1460, 1250, 700 3330, 2950, 1630, 1560 1460, 1250, 800 |

EXAMPLE 50

Preparation of (−)-1-(2-(2,3-dimethoxyphenyl)heptyl)-3-(2,6-diisopropylpehyl)urea To 0.65 g (2.6 mmol) of (+)-2-(2,3-dimethoxyphenyl)-heptylamine was added dropwise a 5.2 ml of 0.502M toluene solution of 2,6-diisopropylphenyl isocyanate at room temperature and the whole was stirred overnight. The reaction mixture was concentrated and the resulting residue was crystallized from methanol. The crystals were collected by filtration and washed with n-hexane to give 0.512 g (43.5% yield) of (+)-1-(2-(2,3-dimethoxyphenyl)heptyl)-3-(2,6-diisopropylpheyl)urea.

Melting point: 113°-115° C.

IR (KBr) cm$^{-1}$: 3410, 3210, 2950, 1640, 1550, 1470, 1270, 1060, 800

NMR (CDCl$_3$) δ: 0.80 (t, 3H), 1.08-1.24 (m, 16H), 1.50-1.61 (m, 2H), 3.09-3.27 (m, 4H), 3.40-3.57 (m, 1H), 3.56 (s, 3H), 3.80 (s, 3H), 4.24 (br. s, 1H), 5.55 (s, 1H), 6.59 (d, 1H), 6.71 (d, 1H), 6.90 (t, 1H), 7.13 (d, 2H), 7.29 (t, 1H)

Optical rotation: $[\alpha]_D^{24} = +0.64$ (c=2.67, methanol)

EXAMPLE 51

Preparation of (−)-1-(2-(2,3-dimethoxyphenyl)heptyl)-3-(2,6-diisopropylpheyl)urea The title compound was prepared in a similar manner to Example 50 using (−)-2-(2,3-dimethoxypehnyl)heptylamine instead of (+)-2-(2,3-dimethoxyphenyl)heptylamine. Yield: 64%.

Melting point: 115°-116° C.

IR (KBr) cm$^{-1}$: 3410, 3210, 2950, 1640, 1550, 1470, 1270, 1060, 800

NMR (CDCl$_3$) δ: 0.80 (t, 3H), 1.08-1.24 (m, 16H), 1.50-1.61 (m, 2H), 3.09-3.27 (m, 4H), 3.40-3.57 (m, 1H), 3.56 (s, 3H), 3.80 (s, 3H), 4.24 (br. s, 1H), 5.55 (s, 1H), 6.59 (d, 1H), 6.71 (d, 1H), 6.90 (t, 1H), 7.13 (d, 2H), 7.29 (t, 1H)

Optical rotation: $[\alpha]_D^{24} = -0.83$ (c=2.64, methanol)

TEST EXAMPLE 1

The effect of reducing a lipid level in blood by the action of the compounds according to the present invention was determined as follows:

Male golden Syrian hamsters weighing from 80 to 100 g were randomly divided into groups. The hamsters were first fed standard laboratory diets (solid feed MF-1 for mouse/rat/hamster, manufactured by Oriental Yeast Industries, KK) for 3 days. Then, they were fed the experimental diet containing 1% cholesterol and 0.5% cholic acid (manufactured by Oriental Yeast Industries, KK), ad libitum. At the same time, the compounds of the invention formulated in a shown dose (0.1-10 mg/10 ml water/kg) were administrated to the animals orally once a day at a determined time for 5 days. Water was administrated orally to the hamsters of control group in an amount of 10 ml per 1 kg of body weight. After five days of administrating the compounds, the animals were anesthetized with Pentobarbital Na (Nembutal injection, manufactured by Dainabbot) and three hours after the final administration of the test compound, a blood sample was taken from abdominal cava. The serum was separated from the sample by centrifuging.

The cholesterol level in the serum was determined by using a blood cholesterol measuring kit, Determina-TC5 manufactured by Kyowa Medix Co. The results are represented by percent inhibition (%) of cholesterol level in serum relative to that of the control group, and shown in the following Table 2.

TABLE 2

| Compound (Example No.) | Percent inhibition of cholesterol in serum (%) | | |
|---|---|---|---|
|  | 5 mg/kg | 1 mg/kg | 0.1 mg/kg |
| 9 |  | 19 |  |
| 12 |  | 43 |  |
| 15 |  | 36 |  |
| 19 |  | 36 |  |
| 24 |  | 39 |  |
| 29 |  | 36 |  |
| 32 |  | 43 |  |
| 33 |  |  | 24 |
| 36 |  | 26 |  |
| 40 |  | 38 |  |
| 49 | 33[2] |  |  |
| 50 |  |  | 18 |
| 51 |  |  | 25 |
| Comparative Example 1[1] | 5 |  |  |

[1] 1-(3,3-dimethyl-2-phenylbutyl)-3-(2,6-diisopropyl-phenyl)urea described in Japanese Patent Application Laying-Open (Kokai) No. 6456/90
[2] 10 mg/kg

TEST EXAMPLE 2

The ACAT inhibitory action of the compounds according to the present invention was measured as follows:

ACAT activity in the hamster microsomes was determined by measuring the rate of radio-active cholesteryl-[$^{14}$C] oleate formation from cholesterol and radio-labelled oleoyl coenzyme A ($^{14}$C) with or without test compound.

Calculations of IC$_{50}$ value were made using data of the percent inhibition at each compound concentration. The results are shown in the following Table 3.

TABLE 3

| Compound (Example No.) | ACAT inhibitory activity IC$_{50}$ (nM) |
|---|---|
| 9 | 4.9 |
| 12 | 26 |
| 33 | 16 |
| 40 | 31 |

What is claimed is:

1. A 1-phenylalkyl-3-phenylurea derivative represented by the following formula (I):

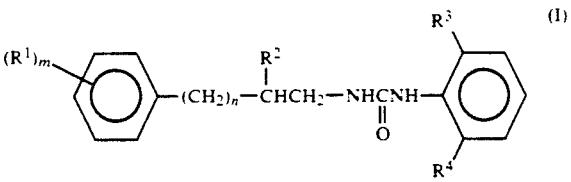

wherein $R^1$ is an alkyl group of 1 to 5 carbon atoms, an alkoxy group of 1 to 5 carbon atoms or a halogen atom, $R^2$ is an alkyl group of 4 to 6 carbon atoms, each of $R^3$ and $R^4$ is independently an alkyl group of 1 to 3 carbon atoms, m is an integer of 1 to 3, and n is 0 or 1.

* * * * *